(12) United States Patent
Yoshikawa et al.

(10) Patent No.: US 10,543,227 B2
(45) Date of Patent: Jan. 28, 2020

(54) HAIR GROWTH COMPOSITION

(71) Applicant: RIKEN, Wako-shi, Saitama (JP)

(72) Inventors: Takeo Yoshikawa, Wako (JP); Motoko Maekawa, Wako (JP); Tetsuo Ohnishi, Wako (JP)

(73) Assignee: Riken, Saitama (JP)

( * ) Notice: Subject to any disclaimer, the term of this patent is extended or adjusted under 35 U.S.C. 154(b) by 0 days.

(21) Appl. No.: 15/766,071

(22) PCT Filed: Oct. 7, 2016

(86) PCT No.: PCT/JP2016/079973
§ 371 (c)(1),
(2) Date: Sep. 14, 2018

(87) PCT Pub. No.: WO2017/061610
PCT Pub. Date: Apr. 13, 2017

(65) Prior Publication Data
US 2019/0015447 A1   Jan. 17, 2019

(30) Foreign Application Priority Data
Oct. 7, 2015   (JP) .................................. 2015-199432

(51) Int. Cl.
A61K 33/04   (2006.01)
A61Q 7/00    (2006.01)
A61K 8/23    (2006.01)
A61P 17/14   (2006.01)

(52) U.S. Cl.
CPC ................ A61K 33/04 (2013.01); A61K 8/23 (2013.01); A61P 17/14 (2018.01); A61Q 7/00 (2013.01)

(58) Field of Classification Search
CPC .. A61K 33/04; A61K 8/23; A61Q 7/00; A61P 17/14
See application file for complete search history.

(56) References Cited

FOREIGN PATENT DOCUMENTS

| CN | 101019868 A | 8/2007 |
|----|-------------|--------|
| JP | 2012-092079 A | 5/2012 |
| JP | 2013-193985 A | 9/2013 |
| JP | 2014-129383 A | 7/2014 |
| JP | 2014-218479 A | 11/2014 |

OTHER PUBLICATIONS

International Search Report dated Nov. 29, 2016, in PCT/JP2016/079973.

Primary Examiner — Shirley V Gembeh
(74) Attorney, Agent, or Firm — Foley & Lardner LLP

(57) ABSTRACT

The invention of this application relates to a composition for growing hairs comprising, as an active ingredient, thiosulfuric acid or a salt thereof that has hair growing effects and has no side effects.

7 Claims, 4 Drawing Sheets

HAIR GROWTH COMPOSITION

CROSS-REFERENCE TO RELATED APPLICATIONS

This application is a National Stage application of PCT/JP2016/079973, filed Oct. 7, 2016, which claims priority from Japanese application JP 2015-199432, filed Oct. 7, 2015.

TECHNICAL FIELD

The present invention relates to a hair growth composition.

BACKGROUND ART

Recently, many people are troubled with thinning hair, hair loss and baldness caused by, e.g., mental stress, changing eating habits, and aging. Because of this, the scalp-care market tends to expand. Such tendency is found in not only men but also women. Normal human hair periodically comes off and grows again. Such a hair cycle is repeated. About 90% of hair is in the anagen phase (i.e., the phase in which hair grows); whereas, about 10% of hair is in the telogen phase (i.e., the phase in which hair stops growing and falls off). Alopecia is caused by a mechanism where growth of hair follicle cells is suppressed and the hairs supposed to be in the anagen phase get in the telogen phase.

As male-pattern hair loss, male-pattern alopecia and alopecia areata are generally known well; while, as female-pattern hair loss, diffuse alopecia is known. As a cause of alopecia, not only a genetic cause but also aging, effects of male hormones, poor blood circulation, excessive hair care, heavy use of oral contraceptive, malnutrition, destruction of hair follicle bulb by lymphocytes are pointed out.

As a therapeutic agent for male-pattern alopecia, minoxidil (as an external preparation) and finasteride (as an oral therapeutic agent) are known. Minoxidil has an action to stimulate dermal papilla cells and causes them to secrete a growth factor, which promotes growth of hair matrix cells; while finasteride suppresses the action of type II 5α-reductase to prevent hair follicle miniaturization. As a therapeutic agent for alopecia areata, drugs such as adrenocortical hormone (a steroid), minoxidil and carpronium chloride are known.

The number of patent literatures concerning hair restoring agents and hair tonics is beyond 1,000 with the inclusion of, for example, JP Patent Publication (Kokai) No. 2012-092079 (Patent Literature 1), JP Patent Publication (Kokai) No. 2014-218479 (Patent Literature 2), JP Patent Publication (Kokai) No. 2014-129383 (Patent Literature 3), and JP Patent Publication (Kokai) No. 2013-193985 (Patent Literature 4). However, among drugs presently on the market, drugs effectively improving alopecia are small in number. A satisfactory hair growth effect cannot be usually obtained just by promoting blood circulation, improving scalp metabolism, and changing the hair cycle. As mentioned, overcoming alopecia can be said to be a difficult challenge.

PRIOR ART LITERATURE

Patent Literature

Patent Literature 1: JP Patent Publication (Kokai) No. 2012-092079
Patent Literature 2: JP Patent Publication (Kokai) No. 2014-218479
Patent Literature 3: JP Patent Publication (Kokai) No. 2014-129383
Patent Literature 4: JP Patent Publication (Kokai) No. 2013-193985

SUMMARY OF INVENTION

Problem to be Solved by the Invention

Scalp skin and head hair care products include a hair tonic, a hair restoring agent (or hair restorer), and a hair growing agent (or a trichogenous agent). The hair tonic is a drug simply nourishing hairs. The restoring agent is a drug promoting growth of hair to be longer and thicker, thereby preventing hair loss. However, the hair tonic and hair restoring agent are said to be drugs for neither treating alopecia nor promoting hair growth in hair loss sites. In contrast, the hair growing agent is a drug for promoting the growth of hairs at hair loss sites. The hair growing agents presently on the market in Japan contain minoxidil or finasteride as an active ingredient. However, the hair growth effects provided by these ingredients vary between individuals, and side effects of the ingredients are also known.

An object of the present invention is to provide a hair growing agent that has hair growth effects (or trichogenous effects) and has almost no side effects.

Means to Solve the Problem

The present inventors have now found that hair growth effects are produced by in vivo reduction actions. Based on the finding, the present invention was accomplished.

In short, the present invention contains the following features.

(1) A composition for growing hairs comprising thiosulfuric acid or a salt thereof as an active ingredient.

(2) The composition according to (1), wherein the thiosulfuric acid or salt thereof in the composition has a concentration of from about 1% (w/v) to about 20% (w/v) or more, or from about 0.06 mol/L to about 1.5 mol/L or more.

(3) The composition according to (1) or (2), further comprising other hair growing agent, hair restoring agent, or hair tonic.

(4) The composition according to (3), wherein the other hair growing agent, hair restoring agent, or hair tonic is cysteine and/or minoxidil.

(5) The composition according to any one of (1) to (4), which is for increasing hairs around hairlines.

(6) The composition according to any one of (1) to (5), which is for a scalp skin and head hair cosmetic.

(7) The composition according to any one of (1) to (5), which is for treatment of alopecia.

(8) The composition according to any one of (1) to (7), which is in the form of a solution, a tonic, a liquid, a lotion, a conditioner, a treatment, a spray, a cream, or a gel.

The present specification includes all the contents of the disclosure of JP Patent Application No. 2015-199432 from which t the present application claims the priority.

According to the present invention, the provided is a composition that has hair growth effects (or trichogenous effects) and has almost no side effects, particularly, a hair growth composition having actions to grow/restore/nourish hairs in both anagen phase and telogen phase of the hair cycle.

MODES FOR CARRYING OUT THE INVENTION

Figure 1:
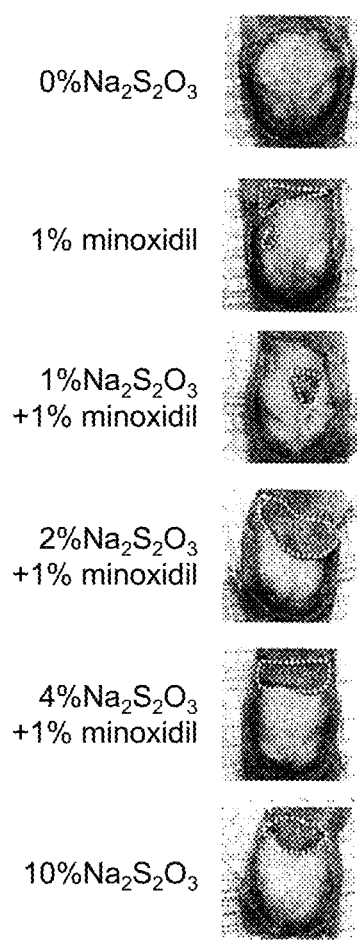
FIG. 1 This figure shows results of hair growth on Day 76 after initiation of application of 10% (w/v) sodium thiosulfate ($Na_2S_2O_3$) and a mixture of 1%, 2% or 4% sodium thiosulfate and 1% minoxidil to hair-shaved back sites of C3H/HeN mice. As a negative control, 0% sodium thiosulfate was applied to hair-shaved back sites of the same mice, and, as a positive control, 1% minoxidil was applied to hair-shaved back sites of the same mice. The head regions at which hair growth was observed are enclosed by dashed lines.

The present invention will be more specifically described.

The present invention provides a composition for growing hairs (or new hairs) comprising thiosulfuric acid or a salt thereof as an active ingredient. Hereinafter, we will describe: the active ingredient of the composition; adding other hair growing agent, hair restoring agent or hair tonic; adding other components; and forms of the composition.

1. Active Ingredient

The active ingredient of the composition of the present invention is thiosulfuric acid or a salt thereof.

The salt of thiosulfuric acid is a salt formed from thiosulfuric acid and a pharmaceutically acceptable base. Examples of the base include inorganic bases and organic bases. Example of the salt include: alkali metal salts of thiosulfuric acid such as sodium thiosulfate or potassium thiosulfate; or ammonium salt of thiosulfuric acid and ammonia, and ammonium salts of thiosulfuric acid and aliphatic amine or cyclic amine. Examples of the aliphatic amine or cyclic amine include triethylamine, triethanolamine, diethanolamine, ethylenediamine, diisopropylamine, amino acids (such as arginine, lysine, tryptophan, and histidine), and pyridine. A preferable salt is sodium thiosulfate.

The thiosulfuric acid or salt thereof is contained in the composition of the present invention in an appropriate amount (or "an effective amount") at which effects of growing, restoring and/or nourishing hairs (for example, hair growth promoting effects) are observed. The concentration of the thiosulfuric acid or salt is usually from about 1-2% (w/v) to about 20% (w/v) or more, preferably from about 3% (w/v) to about 15% (w/v), and further preferably from about 4% (w/v) to about 10% (w/v); or alternatively, from about 0.10 mol/L to about 1.5 mol/L or more; however, the concentration is not limited to these.

It has been neither known nor suggested, before the present application was filed, that substantially non-toxic thiosulfuric acid or a salt thereof has an action to promote the growth of hairs and actions to grow/restore/nourish hairs in both the anagen and telogen phases of the hair cycle.

It was known that salts of thiosulfuric acid (or thiosulfates) can be used as additives for softening water to enhance washing effects, in a hair restoring agent or hair tonic and in a method for restoring or nourishing hair by washing hairs with a washing solution containing micro bubbles (International Publication No. WO 2009/142200); and they can be used as additives having antioxidative effects in hair restoring agents containing vitamin A and a related compound thereof as a primary ingredient (JP Patent Publication (Kokai) No. 2001-199843). However, it was not known that a composition containing thiosulfuric acid or a salt thereof in a predetermined concentration or higher concentration can serve as a hair growing agent.

The thiosulfuric acid or salt thereof is preferably applied to the scalp skin of a person in an effective amount, for example, in a concentration of from about 2% (w/v) to 20% (w/v) or more, once or a plurality of times per day. The thiosulfuric acid or salt thereof has a property of effectively increasing hairs (or new hairs) around the hairlines of a person.

2. Other Hair Growing Agent, Hair Restoring Agent or Hair Tonic

To the composition of the present invention, other hair growing agent and/or other hair restoring agent or hair tonic may be added.

The other hair growing agent that can be used in the present invention includes, but is not limited to, for example a vasodilator. Examples of the vasodilator include minoxidil and minoxidil analogs (e.g., pidioxyzil).

Examples of the other hair restoring agent and hair tonic include, but are not limited to, cysteine, 6-benzylaminopurine, pentadecanoic acid glyceride, carpronium chloride, t-flavanon, dipotassium glycyrrhizinate, sodium polyphosphate, and *Swertia* extract.

The other hair growing agents and/or other hair restoring agent or hair tonic may be used singly or in combination of two or more agents. The content of these auxiliary components is, for example, from 0.01% (w/v) to 20% (w/v) or more, preferably from 0.1% (w/v) to 10% (w/v), in total relative to the composition.

Combination of thiosulfuric acid or a salt thereof and minoxidil synergistically improves hair growth effects. For example, in the combination, the content of the thiosulfuric acid or a salt thereof in total relative to the composition includes, but is not limited to, from 1% (w/v) to 20% (w/v) or more, preferably from 1.5% (w/v) to 15% (w/v) and further preferably from 2% (w/v) to 10% (w/v); or alternatively, from about 0.06 mol/L to about 1.5 mol/L or more.

3. Other Components

The composition of the present invention can further contain one or two or more of an antioxidant, an anti-inflammatory agent, a ultraviolet inhibitor, a keratolytic agent, a blood circulation promoter, a cell activator, a disinfectant, an antiseborrheic agent, a percutaneous absorption enhancer, a refreshing agent, a fragrance, a surfactant, a pH modifier, an excipient, a solubilizer, amino acids, vitamins, colorants, etc. Each of the contents of these components relative to the composition is, for example, from 0.0001% (w/v) to 70% (w/v) or more.

Examples of the antioxidant include vitamin E, tocopherol acetate, d-δ-tocopherol, butylhydroxytoluene, vitamin C, L-ascorbic acid 2-sulfate, L-ascorbic acid 2-phosphate, L-ascorbic acid 2-glucoside, tetraisopalmitic acid, L-ascorbic acid, sodium thioglycolate, polyphenol, and catechin.

Examples of the anti-inflammatory agent include β-glycyrrhetinic acid, glycyrrhizinate, tranexamic acid, glycyrrhizin, licorice, cork tree bark, a *Hypericum* extract, a *Scutellaria* extract, and a moutan bark extract.

Examples of the ultraviolet inhibitor include octyl methoxycinnamate, oxybenzone, and urocanic acid.

Examples of the keratolytic agent include salicylic acid, resorcin, and the like.

Examples of the blood circulation promoter include benzyl nicotinate, nicotinic acid amide, carpronium chloride, acetic acid nicotinate, tocopherol acetate, nonanoic acid vanillylamide, diazoxide, cepharanthin, an iodized garlic extract, Swertiamarin, a capsicum tincture, a gingko extract, a peony extract, and *Swertia* extract.

Examples of the cell activator include hinokitiol, pyridoxine hydrochloride, pantothenyl alcohol, acetyl pantothenyl ethyl ether, biotin, allantoin, pentadecanoic acid glyceride, ethinyl estradiol, placenta extract, a coleus extract, a ginseng extract, adenosine, hinokitiol, and piroctone olamine.

Examples of the percutaneous absorption enhancer include polyalkylene glycols such as polyethylene glycol and polypropylene glycol, and fatty acid esters such as ethyl oleate and octyldodecyl lactate.

Examples of the refreshing agent include menthol, menthyl glyceryl ether, menthyl carboxamide, vanillyl butyl ether, menthone, camphor, borneol, cineole menthone, methyl salicylate, menthyl malonate, 3-1-menthoxypropane-1,2-diol, 1-menthyl-3-hydroxybutyrate, spearmint oil, peppermint oil, mint oil, and eucalyptus oil.

Examples of the fragrance include fragrances for hair cosmetics described in, e.g., JP Patent Publication (Kokai) No. 2002-284660. Specifically, examples of the fragrance include 3-(4-tert-butylphenyl)-propanal, acetyl cedrene, 5-hexyldihydro-5-methyl-2(3H)-furanon, acetaldehyde 2-phenyl-2,4-pentanediol acetal, oxacyclohexadecen-2-one, α-hexyl cinnamic aldehyde, 2,6,10-trimethyl-9-undecenal, dodecahydro-3a,6,6,9a-tetramethylnaphtho(2,1-b)furan, 1-(1,2,3,4,5,6,7,8-octahydro-2,3,8,8-tetramethyl-2-naphthalenyl)-ethanone, 1-(1,2,3,4,5,6,7,8-octahydro-2,3,5,5-tetramethyl-2-naphthalenyl)-ethanone, 4-(4-methyl-3-penten-1-yl)-3-cyclohexenone-1-carboxaldehyde, α-irone, cyclopentadecanolide, 2-methyl-3-(4-t-butylphenyl)propanal, 2-methyl-3-(4-isopropylphenyl)propanal, 2-propenyl-cyclohexyloxyacetate, 1-(2-benzofuranyl)-ethanone, heliotropin, β-ionone, γ-methylionone, 3-(3-isopropylphenyl)butanal, dodecanal, γ-undecalactone, 3-methylcyclopentadecenone, 1-(3-methyl-2-benzofuranyl)-ethanone, β-damascenone, β-damascone, δ-damascone, and methyl 2-pentyl-3-oxo-cyclopentyl acetate.

Examples of the solubilizer include purified water, distilled water, ethanol, polyhydric alcohol, and mixtures thereof.

As the excipient, excipients for pharmaceutical use and for cosmetic use can be employed. For example, pharmaceutically or cosmetically acceptable components such as a solution, an emulsifier, a gelling agent and an aerosol can be used.

Examples of the vitamins include vitamin A, vitamin B, vitamin C, vitamin E, and tocopherol acetate.

4. Form of Composition

The composition of the present invention is any composition for scalp skin/head hair for promoting growth of head hairs. Specifically, examples of the composition include a cosmetic composition for scalp skin/head hair, a therapeutic composition for alopecia, and the like.

The composition may be in the form of a liquid, or a solid or a semisolid. Examples of the form include a solution(s), a tonic(s), a liquid(s), a lotion(s), a conditioner(s), a treatment(s), a spray(s), a cream(s), and a gel(s). Specifically, the composition may be blended in hair dressings, shampoos, rinses, hair colors, permanent agents, hair restoring agents, hair tonics, etc.

The pH of the composition of the present invention is usually preferably from 4 to 8 and more preferably from 6 to 7.5. The viscosity of the composition can be appropriately selected depending on the above composition forms. As viscosity modifiers, for example hydroxyethylcellulose, hydroxypropylcellulose, hydroxypropylmethylcellulose, xanthan gum, carrageenan, carboxyvinyl polymer, and sodium hyaluronate can be used.

EXAMPLES

The present invention will be specifically described by referring to Examples below; however, it should be noted that the scope of the present invention is not limited by these Examples.

Example 1

<Examination 1 in Telogen Phase Model>

C3H/HeN mice (Charles River Japan (Kanagawa, Japan)) of 6 weeks old, the hair cycle of which repeatedly proceeds anagen phase, catagen phase and telogen phase in this order, were raised for a week for acclimatization. At the age of 7 weeks (the telogen phase is started at the age), hairs on the back were shaved off by an electric clipper and a shaver. After the mice were raised overnight, application of a test solution (200 μL per site) to the hair-shaved site was initiated.

As the test solutions for Test 1, solutions prepared by dissolving sodium thiosulfate (1%, 2% and 4% (w/v)) in 50% aqueous ethanol solution; and a solution prepared by dissolving sodium thiosulfate (10% (w/v)) in 40% aqueous ethanol solution, were used. For Test 2, solutions prepared by dissolving minoxidil (1% (w/v)) and sodium thiosulfate (1%, 2%, 4% (w/v)) in 50% aqueous ethanol solution; solutions prepared by dissolving minoxidil (1% (w/v)) and sodium thiosulfate (10% (w/v)) in 40% aqueous ethanol solution; and a solution prepared by dissolving sodium thiosulfate (10% (w/v)) in 40% aqueous ethanol solution, were used. In these tests, the positive control is minoxidil (1% (w/v)) and the negative control is 0% sodium thiosulfate.

In both of Test 1 and Test 2, each test solution was applied to the hair-shaved back sites of 5-12 mice per group, daily at a frequency of once a day. Hair growth effect was evaluated by photographing a hair-shaved site where new hairs sprouted including its periphery on Day 1, 47, 59 and 76 after initiation of application and visually observing the state of hair growth. Alternatively, where needed, the hair growth effects were evaluated by calculating % hair-growth areas.

The evaluation results of Test 1 and Test 2 are shown in Table 1 and Table 2, respectively. Evaluation results were shown by scores based on the following criteria: when the hair-growth area calculated was 0% or more and less than 10%, score 1 was given; when the hair-growth area calculated was 10% or more and less than 25%, score 2 was given, when the hair-growth area calculated was 25% or more and less than 50%, score 3 was given; when the hair-growth area calculated was 50% or more and less than 75%, score 4 was given; and when the hair-growth area calculated was 75% or more, score 5 was given. FIG. 1 shows examples of the state of hair growth of hair-shaved back sites of mice on Day 76. In the figure, the sites enclosed by dashed lines indicate regions where hair growth was observed.

TABLE 1

| Mouse ID | Days after initiation of application ||||||||||| 
|---|---|---|---|---|---|---|---|---|---|---|---|
| | Day 26 | Day 32 | Day 40 | Day 47 | Day 54 | Day 62 | Day 69 | Day 76 | Day 83 | Day 90 | Day 97 |
| 0%-1 | 0 | 0 | 0 | 0 | 0 | 0 | 0 | 0 | 0 | 0 | 2 |
| 0%-2 | 0 | 0 | 0 | 0 | 0 | 0 | 0 | 0 | 0 | 0 | 0 |
| 0%-3 | 0 | 0 | 0 | 0 | 0 | 0 | 0 | 0 | 0 | 0 | 0 |
| 0%-4 | 0 | 0 | 0 | 0 | 0 | 0 | 0 | 0 | 0 | 0 | 0 |
| 0%-5 | 0 | 0 | 0 | 0 | 0 | 0 | 0 | 0 | 0 | 0 | 2 |
| 0%-6 | 0 | 0 | 0 | 0 | 0 | 0 | 0 | 0 | 0 | 0 | 0 |
| Minoxidil 1%-1 | 0 | 0 | 0 | 0 | 0 | 0 | 0 | 0 | 0 | 0 | 0 |
| Minoxidil 1%-2 | 0 | 0 | 0 | 0 | 0 | 0 | 0 | 0 | 0 | 0 | 3 |
| Minoxidil 1%-3 | 0 | 0 | 0 | 0 | 0 | 0 | 0 | 0 | 0 | 0 | 0 |
| Minoxidil 1%-4 | 0 | 0 | 0 | 0 | 0 | 0 | 0 | 0 | 0 | 0 | 0 |
| Minoxidil 1%-5 | 0 | 0 | 0 | 0 | 0 | 0 | 0 | 0 | 0 | 0 | 2 |
| Sodium thiosulfate 1%-1 | 0 | 0 | 0 | 0 | 0 | 0 | 0 | 0 | 0 | 0 | 0 |
| Sodium thiosulfate 1%-2 | 0 | 0 | 0 | 0 | 0 | 0 | 0 | 0 | 0 | 0 | 2 |
| Sodium thiosulfate 1%-3 | 0 | 0 | 0 | 0 | 0 | 0 | 0 | 0 | 0 | 0 | 0 |
| Sodium thiosulfate 1%-4 | 0 | 0 | 0 | 0 | 0 | 0 | 0 | 0 | 0 | 0 | 0 |
| Sodium thiosulfate 1%-5 | 0 | 0 | 0 | 0 | 0 | 0 | 0 | 0 | 0 | 0 | 0 |
| Sodium thiosulfate 2%-1 | 0 | 0 | 0 | 0 | 0 | 0 | 0 | 0 | 0 | 0 | 0 |
| Sodium thiosulfate 2%-2 | 0 | 0 | 0 | 0 | 0 | 0 | 0 | 0 | 0 | 0 | 0 |
| Sodium thiosulfate 2%-3 | 0 | 0 | 0 | 0 | 0 | 0 | 0 | 0 | 0 | 0 | 0 |
| Sodium thiosulfate 2%-4 | 0 | 0 | 0 | 0 | 0 | 0 | 0 | 0 | 0 | 0 | 0 |
| Sodium thiosulfate 2%-5 | 0 | 0 | 0 | 0 | 0 | 0 | 0 | 0 | 0 | 0 | 0 |
| Sodium thiosulfate 4%-1 | 0 | 0 | 0 | 0 | 0 | 0 | 0 | 0 | 0 | 0 | 4 |
| Sodium thiosulfate 4%-2 | 0 | 0 | 0 | 0 | 0 | 0 | 0 | 0 | 2 | 3 | 3 |
| Sodium thiosulfate 4%-3 | 0 | 0 | 0 | 0 | 0 | 0 | 0 | 0 | 0 | 0 | 0 |
| Sodium thiosulfate 4%-4 | 0 | 0 | 0 | 0 | 0 | 2 | 3 | 4 | 5 | 5 | 5 |
| Sodium thiosulfate 4%-5 | 0 | 0 | 0 | 0 | 0 | 0 | 0 | 0 | 0 | 0 | 0 |
| Sodium thiosulfate 10%-1 | 0 | 0 | 0 | 0 | 2 | 0 | 2 | 0 | 2 | 3 | 4 |
| Sodium thiosulfate 10%-2 | 0 | 0 | 0 | 0 | 2 | 3 | 3 | 4 | 5 | 5 | 5 |
| Sodium thiosulfate 10%-3 | 0 | 0 | 0 | 0 | 0 | 0 | 2 | 2 | 2 | 2 | 2 |
| Sodium thiosulfate 10%-4 | 0 | 0 | 0 | 0 | 0 | 2 | 2 | 2 | 2 | 3 | 5 |
| Sodium thiosulfate 10%-5 | 0 | 0 | 0 | 2 | 2 | 2 | 2 | 3 | 4 | 5 | 5 |

(Note)
Bold letters (underlined) indicate data of individuals with hair-growth area of 50% or more confirmed.

TABLE 2

| Mouse ID | Days after initiation of application ||||||||||
|---|---|---|---|---|---|---|---|---|---|---|
| | Day 27 | Day 34 | Day 41 | Day 48 | Day 54 | Day 61 | Day 69 | Day 76 | Day 83 | Day 90 |
| 0%-1 | 0 | 0 | 0 | 0 | 0 | 0 | 0 | 0 | 0 | 0 |
| 0%-2 | 0 | 0 | 0 | 0 | 0 | 0 | 0 | 0 | 0 | 0 |
| 0%-3 | 0 | 0 | 0 | 0 | 0 | 0 | 0 | 0 | 0 | 0 |
| 0%-4 | 0 | 0 | 0 | 0 | 0 | 0 | 0 | 0 | 0 | 0 |
| 0%-5 | 0 | 0 | 0 | 0 | 0 | 0 | 0 | 0 | 0 | 0 |
| 0%-6 | 0 | 0 | 0 | 0 | 0 | 0 | 0 | 0 | 0 | 0 |
| 0%-7 | 0 | 0 | 0 | 0 | 0 | 0 | 0 | 0 | 0 | 0 |
| 0%-8 | 0 | 0 | 0 | 0 | 0 | 0 | 0 | 2 | 3 | 4 |
| 0%-9 | 0 | 0 | 0 | 0 | 0 | 0 | 0 | 0 | 0 | 0 |
| 0%-10 | 0 | 0 | 0 | 0 | 0 | 0 | 0 | 0 | 0 | 0 |
| 0%-11 | 0 | 0 | 0 | 0 | 0 | 0 | 0 | 0 | 0 | 0 |
| 0%-12 | 0 | 0 | 0 | 0 | 0 | 0 | 0 | 0 | 0 | 0 |
| Minoxidil 1%-1 | 0 | 0 | 0 | 0 | 0 | 0 | 0 | 0 | 0 | 0 |
| Minoxidil 1%-2 | 0 | 0 | 0 | 0 | 0 | 0 | 0 | 2 | 3 | 3 |
| Minoxidil 1%-3 | 0 | 0 | 0 | 0 | 0 | 0 | 0 | 0 | 0 | 0 |
| Minoxidil 1%-4 | 0 | 0 | 0 | 0 | 0 | 0 | 0 | 0 | 0 | 0 |
| Minoxidil 1%-5 | 0 | 0 | 0 | 0 | 0 | 0 | 0 | 2 | 4 | 4 |
| Minoxidil 1%-6 | 0 | 0 | 0 | 0 | 0 | 0 | 0 | 0 | 2 | 3 |
| Minoxidil 1%-7 | 0 | 0 | 0 | 0 | 0 | 0 | 4 | 5 | 5 | 5 |
| Minoxidil 1%-8 | 0 | 0 | 0 | 0 | 0 | 0 | 0 | 0 | 2 | 2 |
| Minoxidil 1%-9 | 0 | 0 | 0 | 0 | 0 | 0 | 0 | 0 | 3 | 4 |
| Minoxidil 1%-10 | 0 | 0 | 0 | 0 | 0 | 0 | 0 | 0 | 0 | 0 |
| Minoxidil 1% + sodium thiosulfate 1%-1 | 0 | 0 | 0 | 0 | 0 | 0 | 0 | 2 | 3 | 4 |
| Minoxidil 1% + sodium thiosulfate 1%-2 | 0 | 0 | 0 | 0 | 0 | 0 | 0 | 0 | 0 | 0 |
| Minoxidil 1% + sodium thiosulfate 1%-3 | 0 | 0 | 0 | 0 | 0 | 0 | 2 | 2 | 2 | 2 |
| Minoxidil 1% + sodium thiosulfate 1%-4 | 0 | 0 | 0 | 0 | 0 | 0 | 0 | 0 | 0 | 0 |
| Minoxidil 1% + | 0 | 0 | 0 | 0 | 0 | 0 | 0 | 0 | 0 | 0 |

TABLE 2-continued

| Mouse ID | Day 27 | Day 34 | Day 41 | Day 48 | Day 54 | Day 61 | Day 69 | Day 76 | Day 83 | Day 90 |
|---|---|---|---|---|---|---|---|---|---|---|
| sodium thiosulfate 1%-5 | | | | | | | | | | |
| Minoxidil 1% + sodium thiosulfate 2%-1 | 0 | 0 | 0 | 0 | 0 | 2 | 3 | 3 | 4 | 4 |
| Minoxidil 1% + sodium thiosulfate 2%-2 | 0 | 0 | 0 | 0 | 0 | 0 | 0 | 0 | 0 | 0 |
| Minoxidil 1% + sodium thiosulfate 2%-3 | 0 | 0 | 0 | 0 | 0 | 0 | 0 | 0 | 0 | 0 |
| Minoxidil 1% + sodium thiosulfate 2%-4 | 0 | 0 | 0 | 3 | 4 | 5 | 5 | 5 | 5 | 5 |
| Minoxidil 1% + sodium thiosulfate 2%-5 | 0 | 0 | 0 | 0 | 0 | 2 | 3 | 4 | 4 | 4 |
| Minoxidil 1% + sodium thiosulfate 4%-1 | 0 | 0 | 0 | 0 | 0 | 0 | 2 | 2 | 3 | 3 |
| Minoxidil 1% + sodium thiosulfate 4%-2 | 0 | 0 | 0 | 0 | 0 | 0 | 0 | 0 | 0 | 0 |
| Minoxidil 1% + sodium thiosulfate 4%-3 | 0 | 0 | 0 | 2 | 3 | 4 | 5 | 5 | 5 | 5 |
| Minoxidil 1% + sodium thiosulfate 4%-4 | 0 | 0 | 0 | 0 | 0 | 0 | 3 | 3 | 3 | 3 |
| Minoxidil 1% + sodium thiosulfate 4%-5 | 0 | 0 | 0 | 0 | 0 | 2 | 3 | 3 | 4 | 4 |
| Minoxidil 1% + sodium thiosulfate 10%-1 | 0 | 0 | 2 | 2 | 3 | 5 | 5 | 5 | 5 | 5 |
| Minoxidil 1% + sodium thiosulfate 10%-2 | 0 | 0 | 0 | 0 | 2 | 3 | 3 | 3 | 4 | 5 |
| Minoxidil 1% + sodium thiosulfate 10%-3 | 0 | 2 | 2 | 3 | 3 | 3 | 4 | 5 | 5 | 5 |
| Minoxidil 1% + sodium thiosulfate 10%-4 | 0 | 2 | 3 | 4 | 5 | 5 | 5 | 5 | 5 | 5 |
| Minoxidil 1% + sodium thiosulfate 10%-5 | 0 | 2 | 3 | 3 | 3 | 4 | 4 | 5 | 5 | 5 |
| Sodium thiosulfate 10%-1 | 0 | 0 | 0 | 0 | 2 | 2 | 2 | 2 | 2 | 3 |
| Sodium thiosulfate 10%-2 | 0 | 0 | 0 | 2 | 2 | 2 | 4 | 4 | 4 | 5 |
| Sodium thiosulfate 10%-3 | 0 | 0 | 2 | 2 | 2 | 3 | 3 | 3 | 3 | 4 |
| Sodium thiosulfate 10%-4 | 0 | 0 | 0 | 0 | 2 | 2 | 3 | 3 | 3 | 3 |
| Sodium thiosulfate 10%-5 | 0 | 0 | 0 | 0 | 2 | 2 | 3 | 3 | 3 | 3 |
| Sodium thiosulfate 10%-6 | 0 | 0 | 0 | 0 | 3 | 4 | 4 | 5 | 5 | 5 |
| Sodium thiosulfate 10%-7 | 0 | 0 | 0 | 0 | 0 | 2 | 3 | 3 | 4 | 5 |
| Sodium thiosulfate 10%-8 | 0 | 0 | 0 | 2 | 2 | 2 | 3 | 3 | 4 | 5 |
| Sodium thiosulfate 10%-9 | 0 | 0 | 0 | 0 | 0 | 0 | 2 | 2 | 3 | 3 |
| Sodium thiosulfate 10%-10 | 0 | 0 | 0 | 2 | 2 | 3 | 4 | 5 | 5 | 5 |

(Note)
Bold letters (underlined) indicate data of individuals with hair-growth area of 50% or more confirmed.

From the results of Table 1, Table 2 and FIG. 1, it was confirmed that, in the application case of sodium thiosulfate alone (4% (w/v) or more) and in the mixture application case of sodium thiosulfate and minoxidil (a test solution containing 2% (w/v) or more of sodium thiosulfate), compared to the negative control, the new hairs in the hair-shaved back sites of mice started growing at early stage after the application, and the clear tendency of increasing a hair-growth area was observed. In most cases, hair growth around the hairlines was observed.

Figure 2:
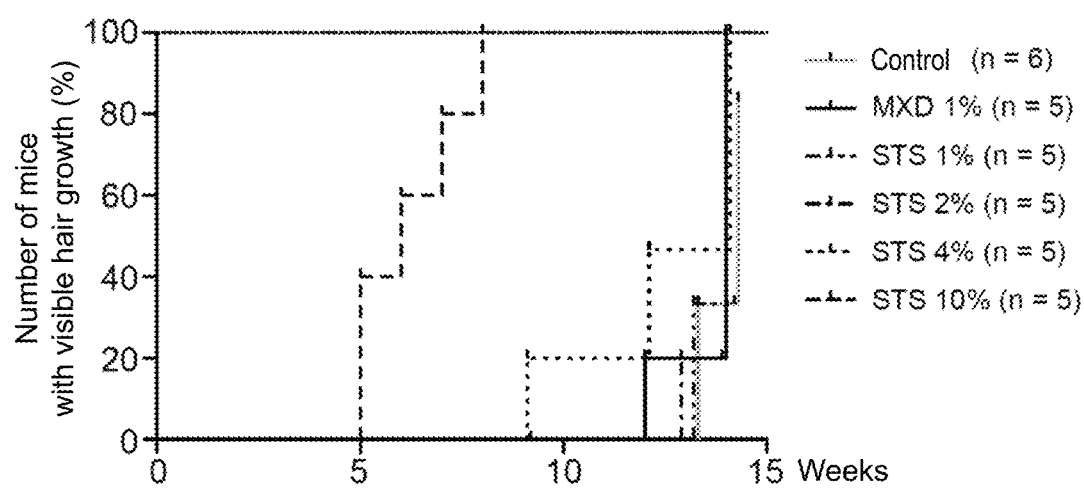
FIG. 2 This figure shows the results of Test 1 of Example 1 expressed by Kaplan-Meier curves in order to evaluate for the time points when hairs start growing. The horizontal axis is the time (weeks) from initiation of application of each drug. The vertical axis is the number of mice (in percentage) in which hair growth was visually observed. The control ("Control") represents a negative control. "MXD" represents minoxidil. "STS" represents sodium thiosulfate. The number of mice used in the test is represented by "n".
Figure 3:
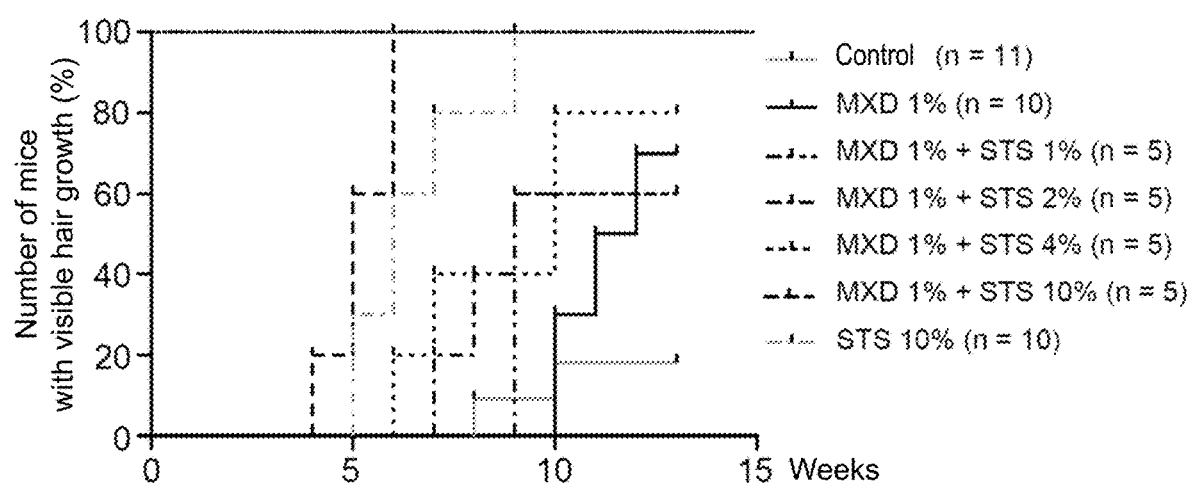
FIG. 3 This figure shows the results of Test 2 of Example 1 expressed by Kaplan-Meier curves in order to evaluate for the time points when hairs start growing. The horizontal axis is the time (weeks) from initiation of application of each drug. The vertical axis is the number of mice (in percentage) in which hair growth was visually observed. The control ("Control") represents a negative control. "MXD" represents minoxidil. "STS" represents sodium thiosulfate. The number of mice used in the test is represented by "n".

Next, with regard to the test results, Kaplan-Meier curves were prepared to evaluate which group new hairs started growing most early. The evaluation results are shown in FIGS. 2 and 3. It was found that as the concentration of sodium thiosulfate increases, new hairs tend to start growing from the earlier stage.

Example 2

<Examination 2 in Telogen Phase Model>

To examine changes in skin symptom by applying sodium thiosulfate to the mice, individual test drugs (i.e., solutions prepared by dissolving sodium thiosulfate (10% (w/v)) in 40% aqueous ethanol solution, and solutions prepared by dissolving minoxidil (1% (w/v)) and sodium thiosulfate (10% (w/v)) in 40% aqueous ethanol solution) were applied to mice shaved in the same manner as in Example 1 and the effect of mixture application was examined. Each test drug was applied to hair-shaved back sites (in an amount of 200 μL per site) of 5-6 animals per group, daily at a frequency of once a day. At 10 minutes and 30 minutes after the application on Day 20, average body surface temperature (° C.) was measured. In these tests, the positive control was minoxidil (1% (w/v)), and the negative control was 0% sodium thiosulfate. Body surface temperature (° C.) was measured by photographing a hair-shaved site and its periphery using an infrared thermography camera (Thermoshot F30S (NEC/Avio, Tokyo, Japan)). The average body surface temperature per area was calculated using InfRec Analyzer NS9500 Standard (NEC/Avio, Tokyo, Japan).

The results are shown in Table 3.

TABLE 3

| Mouse ID | 10 minutes | 30 minutes |
|---|---|---|
| 0%-1 | 37.2(° C.) | 37.3(° C.) |
| 0%-2 | 36.3 | 36.8 |
| 0%-3 | 36.5 | 37 |
| 0%-4 | 36.9 | 36.6 |
| 0%-5 | 36 | 36.7 |
| 0%-6 | 36.4 | 37.2 |

TABLE 3-continued

| Mouse ID | 10 minutes | 30 minutes |
|---|---|---|
| Minoxidil 1%-1 | 36.7 | 37.1 |
| Minoxidil 1%-2 | 36.6 | 37 |
| Minoxidil 1%-3 | 35.9 | 36.7 |
| Minoxidil 1%-4 | 35.6 | 36.6 |
| Minoxidil 1%-5 | 35.3 | 36.7 |
| Sodium thiosulfate 10%-1 | 36.6 | 37.1 |
| Sodium thiosulfate 10%-2 | 36.3 | 36.6 |
| Sodium thiosulfate 10%-3 | 35.8 | 37 |
| Sodium thiosulfate 10%-4 | 35.5 | 37.2 |
| Sodium thiosulfate 10%-5 | 36.7 | 37.2 |
| Minoxidil 1% + sodium thiosulfate 10%-1 | 36.4 | 37 |
| Minoxidil 1% + sodium thiosulfate 10%-2 | 36.4 | 37.1 |
| Minoxidil 1% + sodium thiosulfate 10%-3 | 36.4 | 37.3 |
| Minoxidil 1% + sodium thiosulfate 10%-4 | 36 | 36.8 |
| Minoxidil 1% + sodium thiosulfate 10%-5 | 35.8 | 37 |

As shown in Table 3, the body surface temperature of the mice treated by any of the test drugs was the same as in the negative control. These animals were subjected to drawing blood from the hearts on the final week for biochemical examination. Each blood was allowed to stand still on ice for 30 minutes and centrifuged twice at 10,000 rpm for 15 minutes (at 4° C.). The supernatants (i.e., sera) were transferred to new containers and stored in a freezer (at −80° C.). The sera were analyzed using a clinical chemistry analyzer for animal (FUJI DRI-CHEM 3500V) and special slides to obtain the values of [GPT (glutamate-pyruvate transaminase), GOT (glutamate oxaloacetate transaminase), GGT (γ-glutamyl transferase), LDH (lactate dehydrogenase), CHE (cholinesterase), CPK (creatine phosphokinase), ALB (albumin), TP (total protein), TCHO (total cholesterol), and TG (triglyceride)].

The results are shown in Table 4.

TABLE 4

| Mouse ID | 0% | Minoxidil 1% | Sodium thiosulfate 10% | Minoxidil 1% + Sodium thiosulfate 10% |
|---|---|---|---|---|
| N (Number of animals) | 6 | 5 | 5 | 5 |
| GPT (ALT) (U/l) | 21.5 ± 3.4 | 22.8 ± 4.3 | 20.8 ± 2.3 | 22.8 ± 4.6 |
| GOT (AST) (U/l) | 74.8 ± 20.5 | 66.8 ± 40.2 | 83.2 ± 46.3 | 63.2 ± 28.6 |
| GGT (U/l) | 1.2 ± 0.4 | 1.0 ± 0.0 | 1.0 ± 0.0 | 1.2 ± 0.4 |
| LDH (U/l) | 283.2 ± 53.8 | 237.8 ± 101.6 | 277.4 ± 142.6 | 255.4 ± 142.1 |
| CHE (U/l) | 20.0 ± 3.1 | 16.6 ± 1.5 | 19.8 ± 3.1 | 16.3 ± 1.5 |
| CPK (U/l) | 375.2 ± 114.7 | 321.6 ± 231.5 | 608.4 ± 642.5 | 420.0 ± 330.0 |
| ALB (g/dl) | 2.1 ± 0.2 | 2.2 ± 0.1 | 2.2 ± 0.1 | 2.1 ± 0.2 |
| TP (g/dl) | 4.7 ± 0.1 | 4.7 ± 0.5 | 4.8 ± 0.3 | 4.4 ± 0.2 |
| TCHO (mg/dl) | 161.5 ± 16.3 | 167.2 ± 19.3 | 155.0 ± 10.1 | 160.0 ± 15.4 |
| TG (mg/dl) | 310.2 ± 44.2 | 294.0 ± 44.1 | 296.8 ± 95.5 | 290.6 ± 76.5 |

The above results shows values of biochemical examination having no significant difference in comparison with those of the negative control in any test drug. From the results, it was confirmed that the composition of the present invention has less side effect.

Example 3

(Examination 1 in Anagen Phase Model)

C3H/HeN mice (Charles River Japan) of 6 weeks old were obtained and raised for 5 days for acclimatization. Thereafter, hair was shaved off by a razor with the help of shaving foam. Three days after the hair shaving, application of the test solutions shown below to the hair-shaved sites (in an amount of 200 μL per site) was initiated and continued for 24 days. The effect of the test solutions in the anagen phase was examined (5 groups, and 8 animals per group).

Negative control (Control): 40% aqueous ethanol solution (n=8)

Positive control (5% MXD): 5% minoxidil (w/v) (n=8)

Test solution 1 (4% STS): 4% sodium thiosulfate (w/v) (n=8)

Test solution 2 (10% STS): 10% sodium thiosulfate (w/v) (n=8)

Test solution 3 (10% STS)+(5% MXD): 10% sodium thiosulfate+5% minoxidil (w/v) (n=8)

Test solutions 1, 2, 3 (10% STS) were each dissolved in 40% aqueous ethanol solution. The solution of the positive control and test solution 3 (5% MXD) were each dissolved in 60% aqueous ethanol solution. The effects of the test solutions on hair removal sites were evaluated based on scores given to the following states of the dorsal skin. In the case of Test solution 3, 10% STS was first administered, followed by administration of 5% MXD.

Score 1: skin exhibits pink.

Score 2: skin color changes to gray (less than 30% of hair removal site).

Score 3: skin color changes to gray (less than 60% of hair removal site) or hair growth is observed (less than 30% of hair removal site).

Score 4: skin color changes to gray (60% or more of hair removal site) or hair growth is observed (less than 60% of hair removal site).

Score 5: hair growth is observed (60% or more of hair removal site).

Figure 4:
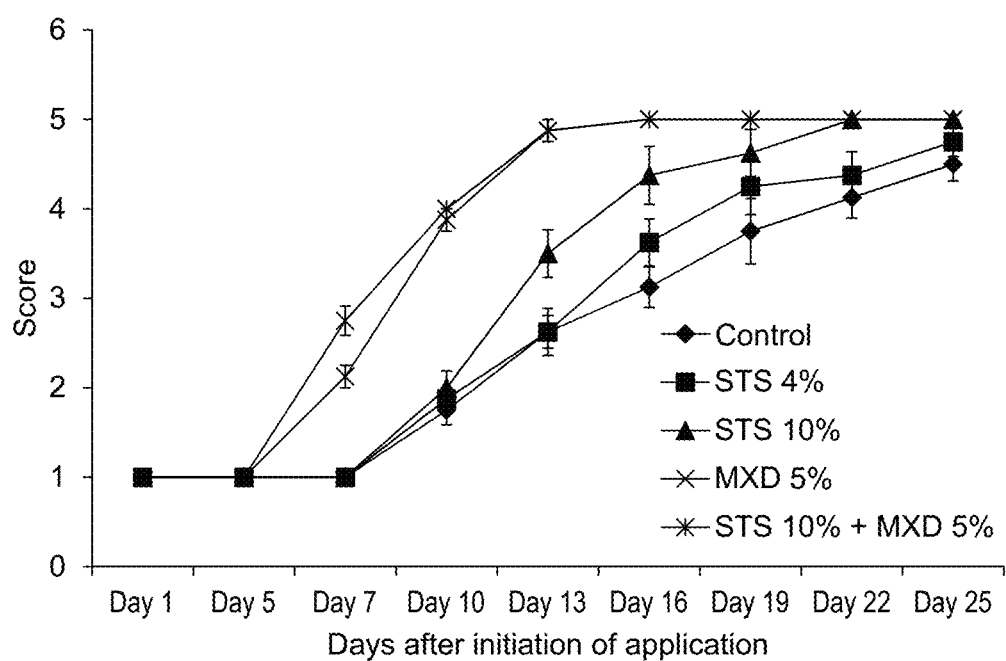
FIG. 4 This figure shows the results of Example 3. The horizontal axis is the time (days) from initiation of application of each drug. The vertical axis is the score determined. The control ("Control") represents a negative control. "MXD" represents minoxidil. "STS" represents sodium thiosulfate.

As a result of the examination, it was confirmed that in the cases of test solutions 1 and 2, hair starts growing earlier than in the negative control. From this, it was demonstrated that the composition of the present invention also acts in the anagen phase (FIG. 4). In the case of test solution 3 (a mixture with minoxidil), hair starts growing earlier than the positive control. From the results, it was further demonstrated that sodium thiosulfate enhances the effect of minoxidil.

Example 4

<Examination 2 in Anagen Phase Model>

After the test in the anagen phase model of Example 3 was completed, a mouse skin tissue of a site where new hairs started growing after hair removal was taken and subjected to histological examination. Specifically, the skin tissue was taken and fixed in 10% neutral buffered formalin. Paraffin sections were prepared, stained with hematoxylin/eosin (HE), and microscopically observed. Hair root density and anagen phase/telogen phase ratio were evaluated. The results are shown in Table 5.

TABLE 5

| (Mouse ID) | Negative control (Control) (n = 8) | Positive control (5% MXD) (n = 8) | Test solution 2 (10% STS) (n = 8) | Test solution 3 (10% STS + 5% MXD) (n = 8) |
|---|---|---|---|---|
| Hair root density (/mm) | 2.34 ± 0.38 | 2.04 ± 0.32 | 2.03 ± 0.23 | 2.11 ± 0.20 |
| Anagen phase/telogen phase | 2.46 ± 3.98 | 0.11 ± 0.05 | 0.25 ± 0.30 | 0.07 ± 0.08 |
| Subcutaneous tissue (mm) | 118.0 ± 71.4 | 38.4 ± 9.0 | 60.5 ± 33.0 | 41.3 ± 19.2 |

In the case of positive control (5% minoxidil), the rate of telogen phase is larger than that of anagen phase. From this result, it is presumed that the phase of the hair cycle transfers from anagen phase to telogen phase. On the other hand, test solutions 2 and 3 of the present invention show the same tendency as in the positive control (Table 5). Particularly, in the case of test solution 3, the effect equal to and larger than in the case of 5% minoxidil was observed. The subcutaneous tissue is thick in the case of positive control (5% minoxidil). The cases of test solutions 2 and 3 of the present invention show the same tendency as in the positive control (Table 5). It was successfully confirmed that the present invention is effective in restoring hair.

Example 5

<Examination 3 in Anagen Phase Model>

After the test in the anagen phase model of Example 3 was completed, a mouse skin tissue of a site where hairs started growing after hair removal was taken and subjected to histopathological examination for toxicity. Specifically, the skin tissue was taken and fixed in 10% neutral buffered formalin. Paraffin sections thereof were prepared, stained with HE, and microscopically observed.

In all cases of the negative control (Control), positive control (5% MXD), test solution 2 (10% STS) and test solution 3 (10% STS+5% MXD), no individuals having tissue abnormality were found. Also in the test in the anagen phase model, it was confirmed that the composition of the present invention has less side effect.

INDUSTRIAL APPLICABILITY

The composition of the present invention provides hair growth effects equal to or larger than minoxidil by applying the hair growth composition to the scalp skin/head hair of a subject (or person) at a frequency of once a day. Thus the composition of the invention is industrially useful.

All publications, patents and patent applications cited in the specification are incorporated herein in their entirety by reference.

The invention claimed is:

1. A composition for growing hairs comprising thiosulfuric acid or a salt thereof as an active ingredient, wherein the thiosulfuric acid or salt thereof in the composition has a concentration of from about 1% (w/v) to about 20% (w/v) or more, or from about 0.06 mol/L to about 1.5 mol/L or more.

2. The composition according to claim 1, further comprising other hair growing agent, hair restoring agent, or hair tonic.

3. The composition according to claim 2, wherein the other hair growing agent, hair restoring agent, or hair tonic is cysteine and/or minoxidil.

4. The composition according to claim 1, which is for increasing hairs around hairlines.

5. The composition according to claim 1, which is for a scalp skin and head hair cosmetic.

6. The composition according to claim 1, which is for treatment of alopecia.

7. The composition according to claim 1, which is in the form of a solution, a tonic, a liquid, a lotion, a conditioner, a treatment, a spray, a cream, or a gel.

* * * * *